(12) United States Patent
Timmins et al.

(10) Patent No.: US 9,453,253 B2
(45) Date of Patent: Sep. 27, 2016

(54) METHODS OF USING ISOTOPICALLY LABELLED ISONIAZID FOR THE DIAGNOSIS OF MYCOBACTERIAL INFECTIONS

(71) Applicants: STC.UNM, Albuquerque, NM (US); THE JOHNS HOPKINS UNIVERSITY, Baltimore, MD (US)

(72) Inventors: Graham Timmins, Albuquerque, NM (US); Seong Choi, Albuquerque, NM (US); Zachary Sharp, Albuquerque, NM (US); Viorel Atudorei, Albuquerque, NM (US); Mamoudou Maiga, Adelphi, MD (US); William Bishai, Towson, MD (US)

(73) Assignees: STC.UNM, Albuquerque, NM (US); THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/404,134

(22) PCT Filed: Mar. 7, 2013

(86) PCT No.: PCT/US2013/029626
§ 371 (c)(1),
(2) Date: Nov. 26, 2014

(87) PCT Pub. No.: WO2013/180779
PCT Pub. Date: Dec. 5, 2013

(65) Prior Publication Data
US 2015/0104819 A1    Apr. 16, 2015

Related U.S. Application Data (60) Provisional application No. 61/653,763, filed on May 31, 2012.

(51) Int. Cl.
| G01N 33/60 | (2006.01) |
| C12Q 1/04 | (2006.01) |
| G01N 33/569 | (2006.01) |
| C12Q 1/28 | (2006.01) |

(52) U.S. Cl.
CPC . *C12Q 1/04* (2013.01); *C12Q 1/28* (2013.01); *G01N 33/5695* (2013.01); *G01N 33/60* (2013.01); *C12Q 2304/48* (2013.01); *G01N 2333/35* (2013.01)

(58) Field of Classification Search
None
See application file for complete search history.

(56) References Cited

U.S. PATENT DOCUMENTS

| 7,717,857 B2 * | 5/2010 | Timmins | A61K 51/04 600/529 |
| 7,897,400 B2 * | 3/2011 | Timmins | A61B 5/0002 436/63 |
| 2004/0224918 A1 | 11/2004 | Yatvin et al. | |
| 2011/0218220 A1 * | 9/2011 | Timmins | A61K 9/0019 514/354 |
| 2015/0246126 A1 * | 9/2015 | Timmins | A61K 41/0052 514/354 |

OTHER PUBLICATIONS

Choi, S. et al. Rapid in vivo Detection of Isoniazid Sensitive *Mycobacterium tuberculosis* by Breath Test. Nature Communications vol. 5 1-6, Sep. 23, 2014.*
Smieja, Marek et al.; Isoniazid for preventing tuberculosis in non-HIV infected persons. The Cochrane Collaboration Jan. 20, 2010; pp. 1-27.
Timmings GS, et al. Nitric oxide generated from isoniazid activation by KatG: source of nitric oxide and activity against *Mycobacterium tuberculosis*. Antimicrob Agents Chemother, 2004;48(8):30006-30009.
Todorovic S, et al. Binding of 15N-labeled isoniazid to KatG and KatG(S315T): Use of Two-Spin [zz]-Order Relaxation Rate for 15 N—Fe Distance Determination. J Am Chem Soc, 1999;121:10962-10966.

* cited by examiner

*Primary Examiner* — Ralph Gitomer
(74) *Attorney, Agent, or Firm* — Henry D. Coleman; R. Neil Sudol (57) ABSTRACT

The present invention is directed to methods of diagnosing the presence or absence of a bacterial infection in a patient, in particular, a tuberculosis infection, by measuring exhaled, isotopically labeled nitrogen gas after administration of isotopically labeled isoniazid.

8 Claims, 7 Drawing Sheets

METHODS OF USING ISOTOPICALLY LABELLED ISONIAZID FOR THE DIAGNOSIS OF MYCOBACTERIAL INFECTIONS

CROSS REFERENCE TO RELATED APPLICATIONS

This application claims the benefit of and is a U.S. national phase application of international patent application no. PCT/US2013/029626 filed 7 Mar. 2013 which claims the benefit of U.S. Provisional Application No. 61/653,763, filed May 31, 2012, the entirety of which two applications is incorporated by reference herein.

TECHNICAL FIELD

The present invention is directed to methods of detecting bacterial infections, in particular, tuberculosis infections, in the lungs of patients by administering isotopically labeled isoniazid and measuring the amount of exhaled isotopically labeled nitrogen gas.

BACKGROUND

Tuberculosis ("TB") is an infection caused by *Mycobacterium tuberculosis* ("*M. tuberculosis*"), a tubercle *bacillus* bacteria. Tuberculosis is a potentially fatal, contagious disease that can affect almost any part of the body but is most frequently an infection of the lungs. The disease is a major cause of mortality and morbidity throughout the world and treatment has been complicated by the emergence of drug-resistant organisms, including multiple-drug resistant tuberculosis, especially in those with HIV infection. While X-rays, sputum cultures, and skin tuberculin testing can be used to diagnose tuberculosis, none of these tests are rapid or highly reliable. As tuberculosis is an airborne disease, it has the potential for bioterror use. In addition, since tuberculosis is contagious, rapid diagnosis of the disease is important for starting treatment as soon as possible to avoid further spread of the disease. As a result, new methods for the rapid diagnosis of tuberculosis are needed.

SUMMARY

The invention is directed to methods for determining the presence or absence of a bacterial infection in the lungs of a patient comprising administering to the lungs of the patient a diagnostically effective amount of 15N-labeled isoniazid and optionally, isotopically labeled urea; collecting one or more samples of exhaled breath from the subject; and determining the amount of 15N-labeled nitrogen gas in said samples; said amount indicating the presence or absence of the bacterial infection in the lungs of the patient. Compositions and kits for use in the methods of the invention are also described.

DETAILED DESCRIPTION OF ILLUSTRATIVE EMBODIMENTS

Isoniazid ("INH") is used to treat tuberculosis.

isoniazid

U.S. Pat. No. 7,897,400, incorporated by reference herein, describes, among other things, the use of isotopically labeled isoniazid and isotopically labeled urea for diagnosing an *M. tuberculosis* infection in the lungs of patients by analyzing exhaled NO, $NO_2$, $NO_3$, CO, and/or $CO_2$ before and after the administration of the isotopically labeled agents. As described in U.S. Pat. No. 7,897,400, *M. tuberculosis* will react with isoniazid in the lungs to produce NO, $NO_2$, $NO_3$, CO, and/or $CO_2$. In addition, *M. tuberculosis* will react with urea in the lungs to produce CO, and/or $CO_2$. After administering isotopically labeled isoniazid to the lungs of the patient, U.S. Pat. No. 7,897,400 teaches that the exhaled breath of the patient can be analyzed for the presence of isotopically labeled NO, $NO_2$, $NO_3$, CO, and/or $CO_2$ and compared to a control sample obtained from the patient prior to the isotopically labeled agent administration. An increase in the amount of isotopically labeled NO, $NO_2$, $NO_3$, CO, and/or $CO_2$ following administration of the isotopically labeled isoniazid and/or isotopically labeled urea is indicative of a *M. tuberculosis* infection.

Moreover, as U.S. Pat. No. 7,897,400 describes, there are strains of *M. tuberculosis* that are resistant to isoniazid and do not react with isoniazid in the lung to produce NO, $NO_2$, $NO_3$, CO, and/or $CO_2$. In such cases, isotopically labeled urea can be administered to the lungs of the patient. In such cases, an increase in the amount of isotopically labeled CO and/or $CO_2$ following administration of the isotopically labeled urea, where isotopically labeled isoniazid administration did not result in an increase in isotopically labeled exhaled gases, is indicative of an isoniazid-resistant *M. tuberculosis* infection.

While U.S. Pat. No. 7,897,400 identified that exhaled NO, $NO_2$, $NO_3$, CO, and/or $CO_2$ following administration of isotopically labeled isoniazid can be used to diagnose the presence or absence of an *M. tuberculosis* infection, it has heretofore been surprisingly and unexpectedly discovered that measuring exhaled nitrogen ($N_2$) following administration of isotopically labeled isoniazid is a more diagnostic method for detecting the presence or absence of an *M. tuberculosis* infection than previously described methods. It has now been discovered that nitrogen gas is a major volatile by product of the exposure of isoniazid to *M. tuberculosis*. Prior to the present disclosure, the conversion in the lungs of isoniazid to $N_2$ by *M. tuberculosis*, and use of this conversion to diagnose the presence or absence of an *M. tuberculosis* infection, was unknown.

Without wishing to be bound by theory, it is believed that isoniazid, after contact with *M. tuberculosis*, and likely the mycobacterial enzyme KatG present therein, in the lungs of a patient, produces nitrogen gas according to the following Scheme 1:

While the present invention is preferably useful for the diagnosis of a tuberculosis infection, any bacteria that convert isoniazid to nitrogen gas can be detected using the methods and compositions described herein.

In light of the mechanism set forth in Scheme 1, isotopically labeling one or both of the nitrogens of isoniazid, preferably both nitrogens, would result in the generation of isotopically labeled nitrogen gas, which can be measured and quantified in order to diagnose the present or absence of an *M. tuberculosis* infection in the lungs of a patient. The methods of the present invention are non-invasive, simple to perform, practical, sensitive, and specific. The validity of the methods is not influenced by stress, exercise, hormone imbalances, or some drugs and medications. As the methods do not involve radioactive compounds, the methods may be used in pediatric populations, as well as adults, with no extraordinary precautions.

Measuring nitrogen gas has several key advantages over measuring other exhaled gases, for example carbon monoxide and nitric oxide. For example, nitrogen gas is unreactive and does not strongly bind to heme proteins, unlike gases such as nitric oxide and carbon monoxide. As a result, more nitrogen gas will be exhaled from the patient, in a more rapid manner, as compared to those gases that bind to heme proteins. In addition, $^{15}N$ isotopic abundance is about 0.346% and the natural abundance of $^{15}N_2$ in air is about 0.0013%. This provides a very low background against which one can sensitively detect $^{15}N_2$ derived from isoniazid that has contacted *M. tuberculosis* in the body.

Within the scope of the invention, the isotopically-labeled isoniazid is labeled at one or both of the hydrazide nitrogens with $^{15}N$:

Isotopically labeled isoniazid can be prepared according to methods described in the art. For example, $^{15}N$-labeled isoniazid can be prepared according to, for example, Timmins, G. S., et al., *Nitric oxide generated from isoniazid activation by KatG: source of nitric oxide and activity against Mycobacterium tuberculosis*, Antimicrob. Agents Chemother. 2004 August; 48(8):30006-9 and Todorovic, S. et al., *Binding of 15N-labeled isoniazid to KatG and KatG (S315T): Use of Two-Spin [zz]-Order Relaxation Rate for 15N-Fe Distance Determination*, J. Am. Chem. Soc. 1999, 121, 10962-10966. For example, $^{15}N$-labeled isoniazid can be prepared according to the following Scheme 3:

Depending on the isotopically labeled isoniazid, the nitrogen byproduct resulting from the reaction of *M. tuberculosis* with the isoniazid is either $^{15}N{=}N$ or $^{15}N{=}N^{15}N$.

Also within the scope of the invention are methods that optionally comprise the administration of isotopically labeled urea [$NH_2C(O)NH_2$]. While an isotopic label can be provided on any atom of urea, it is preferred that the urea is isotopically labeled with $^{13}C$. In embodiments where $^{13}C$-labeled urea is used, *M. tuberculosis* will convert the $^{13}C$-labeled urea to $^{13}C$-labeled carbon monoxide and/or $^{13}C$-labeled carbon dioxide.

Within the scope of the invention, "isotopically labeled" refers to the presence of an isotope, for example $^{13}C$ or $^{15}N$, in a compound that is present in an amount above natural abundance.

Within the scope of the invention, isotopically labeled isoniazid, and optionally isotopically labeled urea, are administered to the patient to be tested for *M. tuberculosis* infection. Depending on the existence and amount of isotopically labeled nitrogen in the exhaled breath of the patient following administration of the isotopically labeled isoniazid, diagnostic information may be used to determine whether or not there is an *M. tuberculosis* infection in the lungs of the patient and whether, if there is an infection, that infection is isoniazid sensitive or isoniazid resistant. Either a single breath or a plurality of breaths may be taken at predetermined times after administration of the isotopically labeled isoniazid, and optionally isotopically labeled urea, can be used to determine the existence or absence of an active *M. tuberculosis* infection and optionally, its sensitivity or resistance to isoniazid.

The ratio of isotopically labeled exhaled gases, for example, isotopically labeled nitrogen gas, isotopically labeled carbon monoxide, and/or isotopically labeled carbon dioxide, to non-isotopically labeled exhaled gases may be determined and compared to a predetermined reference or control value, determined from the patient prior to the administration of isotopically labeled agent, for example, isotopically labeled isoniazid and optionally, isotopically labeled urea. A measurement obtained from the patient that evidences a ratio above the reference ratio will be evidence of the existence of infection and/or sensitivity to isoniazid. A measurement of approximately the reference ratio will be evidence of no infection or inactive *M. tuberculosis* or, in the case of infection that is urea positive, with no activity from isoniazid (isoniazid negative), the existence of an infection with an isoniazid resistant strain of *M. tuberculosis*.

A number of breaths at different times may be taken from the patient and a graph or curve generated showing the ratio of the isotopically labeled gas to the naturally occurring gas in the breath of the patient as a function of time. A curve showing an increase in the ratio of the isotopically labeled gas to non-isotopically labeled gas over time, compared to a control with no infection, is evidence of the existence of an *M. tuberculosis* infection. The concentrations of isotopically labeled gas in the samples are compared to a standard ratio which may be obtained from a control group, or more preferably, from the patient prior to administration of isotopically labeled isoniazid and optionally, isotopically labeled urea.

A curve may be fitted to the measured concentrations and then analyzed, preferably by determined the rate of rise of the curve, or by the magnitude of the plateau. Such an analysis indicates the level of activity of *M. tuberculosis* species in the subject, which can be used to diagnose the presence of *M. tuberculosis* in the lungs, or other tissues, of the subject.

The exhaled breath samples can be obtained in a number of ways including, but not limited to, having the patient exhale or blow into a tube connected to the measuring instrument. Alternatively, a breath collection device such as a bag or vial containing a septum or nasal cannula is used. The patient can breathe directly into the breath collection device. Or, in the case of the nasal cannula that is connected to the measuring instrument, each prong of the nasal cannula can be inserted into a nostril(s) and the subject exhales through the nose, whereby the exhaled air flows through the cannula to the measuring instrument.

The measuring instrument used in the methods of the present invention can be any instrument that can measure amounts of isotopically and non-isotopically labeled gases such as isotopically labeled nitrogen, carbon monoxide, and carbon dioxide. Particularly preferred instruments are mass spectrometer gas analyzers, laser spectrometers, and isotope ratio mass spectrometers. These instruments are well known in the art and are rapid, accurate, and sensitive.

The measuring instrument should be able to measure the concentration of isotopically and non-isotopically labeled gases rapidly. Also, the measuring instrument, or an associated device, should be able to perform the associated analysis, including providing a readout, or in the case where a curve is to be generated, generating the curve and fitting the curve and providing the analysis of the curve. Such analyses will be performed rapidly. Preferably, the measuring instrument, either alone or in conjunction with the associated device, should be able to measure the concentration of isotopically labeled and non-isotopically labeled gases and perform the associated analysis within about 5 minutes, preferably less than 30 seconds.

In embodiments of the invention where isotopically labeled isoniazid is the sole diagnostic composition used, detection of isotopically labeled nitrogen gas is strong evidence of the existence of *M. tuberculosis*, and likely is strongly evidence that the infection may be treated with isoniazid. Lack of detection of isotopically labeled nitrogen gas indicates that the patient is either free of *M. tuberculosis* or that the patient is infected with an isoniazid resistant strain of *M. tuberculosis*.

In embodiments of the invention where both isotopically labeled isoniazid and isotopically labeled urea are administered to a patient to be diagnosed, lack of detection of isotopically labeled nitrogen gas, carbon monoxide, and/or carbon dioxide is strong evidence of the patient being free of *M. tuberculosis*. Detection of isotopically labeled carbon monoxide or isotopically labeled carbon dioxide, but not isotopically labeled nitrogen gas indicates the existence of an isoniazid resistant strain of *M. tuberculosis*. Detection of isotopically labeled nitrogen gas and isotopically labeled carbon monoxide, and/or isotopically labeled carbon dioxide is evidence of existence of a strain of *M. tuberculosis* that may be treated with isoniazid.

As used herein, the term "effective" refers to an amount of isotopically labeled isoniazid, isotopically labeled urea, or a mixture thereof, which is sufficient to produce a detectable level of nitrogen, carbon monoxide, and/or carbon dioxide, without an untoward level of adverse side effects, for example, toxicity, irritation, allergy, or hypersensitivity responses by the patient.

As used herein, the term "coadministration" refers to the administration of at least two active compounds, that is, isoniazid and urea, in effective amounts. Although the term "coadministration" preferably includes the administration of active compounds to the patient at the same time, it is not necessary that the compounds actually be administered simultaneously, only that amounts of compound will be administered to a patient such that effective concentrations of $N_2$, NO, CO, and/or $CO_2$ are found in the exhaled breath.

As used herein, "control ratio" refers to the ratio of isotopically labeled nitrogen, carbon monoxide, or carbon dioxide to non-isotopically labeled nitrogen, carbon monoxide, or carbon dioxide in a sample obtained from a patient prior to administration of isoniazid and/or urea, or a similar ratio obtained from a control population other that the patient.

This fitting and analysis of a curve of measured concentrations may be preferred over other approaches. The present invention, however, allows repeated breath samples to be rapidly obtained either within a single time period or multiple time periods and then maximizes both the speed and accuracy of analysis by providing a one point reference number (for the single time period analysis) above which diagnosis of active infection may be made or, in the case of multiple time periods, fitting the measured values to a curve and then calculating the rate of increase of the curve, which evidences the infection and its intensity.

Any method for identifying the concentration of isotopically gases can be used to determine the existence, or absence, of *M. tuberculosis* in the lungs (or other tissues) of a patient. The measurement of isotopically labeled gas as a cleavage product by action of *M. tuberculosis* on isoniazid and/or urea is evidence of the existence (or absence) of *M. tuberculosis* in the lungs (or other tissues) of the subject or the existence (or absence) of an isoniazid resistant strain of *M. tuberculosis* in the lungs (or other tissues) of the subject. Thus, where both isotopically labeled isoniazid and isotopically labeled urea are administered to a patient to be diagnosed, evidence of cleavage of neither urea nor isoniazid is strong evidence of the subject being *M. tuberculosis* free, evidence of cleavage of urea but not isoniazid indicates the existence of an isoniazid resistant strain of *M. tuberculosis* and evidence of cleavage of both urea and isoniazid is evidence of the existence of a strain of *M. tuberculosis* which may be treated with isoniazid.

In the present invention, it is preferred to determine a ratio of an isotopically labeled element (carbon, nitrogen) to a non-isotopically labeled element in a cleavage product, i.e., carbon monoxide, carbon dioxide, or nitrogen gas) being analyzed. For example, if nitrogen gas ($N_2$) is being measured as a cleavage product pursuant to isoniazid administration, a ratio of nitrogen-15 to nitrogen-14 in nitrogen gas obtained from the breath of a patient is determined. This may be determined readily using mass spectroscopy or infrared laser spectroscopy. In preferred aspects of the invention, a ratio of nitrogen-15 to nitrogen-14 in nitrogen gas exhaled by a subject to be diagnosed before administration of isoniazid is determined as a baseline ratio.

Specifically, an exemplary method of analysis involves the following steps. A plurality of samples of exhaled breath of the subject is collected rapidly, on the order of one sample about every few seconds or so, preferably such that at least a majority, and most preferably substantially all of the exhaled breaths of the subject at a predetermined time for a predetermined period(s) are sampled. Next, the concentration of a cleavage product, for example, nitrogen gas, carbon monoxide, carbon dioxide, is measured and the concentration of an isotopically labeled element, such as nitrogen-15 or carbon-13 is compared with its naturally occurring counterpart (e.g. respectively, nitrogen-14 and carbon-12) in the breath of the subject. Where the ratio of isotopically-labeled element to naturally occurring element is approximately 0 or approximately a control ratio (the control ratio is based upon measurements taken in the subject prior to administration of isotopically labeled isoniazid and/or isotopically labeled urea), then *M. tuberculosis* is not present. In cases where the ratio of isotopically-labeled element to naturally occurring element is above a predetermined value (e.g. established from control groups) measurements above the predetermined value and/or increases of the ratio as a function of time, evidences the existence of *M. tuberculosis*.

Although measuring and analyzing exhaled breaths from a subject for a single predetermined period represents a preferred approach to determining the existence or absence of a *M. tuberculosis* infection, alternative approaches also may be used. In instances where a number of measurements of exhaled breath from the subject are taken from different periods, a curve may be fitted or generated from the measured concentrations. If the ratio remains flat at the x-axis (essentially 0 or close to 0-based upon the subject or a control group) as a function of time, the presence of *M. tuberculosis* can be ruled out. The rate of rise of the curve may be determined by calculating the integral or by derivation (calculation of the derivative), preferably after the measurement of the concentration of cleavage product(s) in each sample. The analysis of the curve indicates the level of *M. tuberculosis* activity in the lungs of the subject. A rapid rise in the measured concentrations (a steeper curve), would evidence a high level of *M. tuberculosis* activity in the subject, whereas a slower rise in the measured concentrations (a shallower curve) would evidence a lower level of *M. tuberculosis* activity. If the *M. tuberculosis* infection is systemic, a greater period of time will be required for absorption and distribution of the labeled compound to the site of infection and release of labeled gasses. The technique will also prove useful in monitoring the responses of the tuberculosis infection to drugs. If the drugs are effective, then the bacterial load (measured as either the rate of isotopically labeled gas increase, or the value of the plateau), will continue to decrease—if the drugs are ineffective due to resistance, then this will not happen and so alternative drug therapies used.

The single point (predetermined time period) approach to diagnostic analysis has a number of advantages, for example, ease of use and rapid diagnosis. The invention also provides diagnostic methods which can be used in a clinic or a doctor's office. A single calculation may be made by taking a number of exhaled breaths from the patient or subject for the predetermined period and then analyzing for isotope-labeled gases in the sample, providing a ratio of isotopically-labeled gases to non-isotopically-labeled gases and comparing that ratio to a predetermined ratio obtained from the patient or from a control group.

In other approaches, the calculation of a derivative from a graph produced from a number of collection samples (from varying time periods) which provides a number of data points has advantages over other methods of analysis, such as the calculation of an integral. First, the calculation of the derivative does not require a reference breath sample to be obtained before isoniazid/urea is administered to the subject. Since the derivative represents the rate of increase of the measured concentrations of a cleavage product or products, for example, nitrogen gas, carbon monoxide, carbon dioxide, the starting concentration of that cleavage product or products is unimportant. However, the initial concentration of the cleavage product or products in the reference breath sample is important for the proper calculation of the integral, since such an initial concentration represents a background value which must be subtracted from the measured concentrations after administration of the isotopically labeled isoniazid and optionally, isotopically labeled urea.

After the resultant measurement has reached a predetermined level of accuracy, or after a predetermined time period has elapsed, no more samples are collected.

The present method utilizing a breath assay has a number of advantages, examples of which are recited here. First, the exhaled breath of the subject can be analyzed in real time; that is, there is relatively little delay between the time the *M. tuberculosis* activity takes place, and the time such activity is measured. Second, the samples of exhaled breath are obtained rapidly and are analyzed immediately in a manner which substantially increases the accuracy of the results. Depending on method, one or multiple samples may be obtained. In general, a single sample (from a number of exhaled breaths) represents a convenient method which exhibits ease of use and patient compliance. In contrast, obtaining multiple samples from the patient increases the accuracy of the test. There is also less statistical error since many samples are collected. In addition, in this aspect, since samples are preferably collected until a preset level of accuracy is reached, ambiguous results can be substantially eliminated, preventing the need for repeating the test.

The readout of isotopic ratios can be performed by, for example, sensitive gas mass spectrometry analysis and laser spectroscopy techniques, which may allow for more compact and portable devices. In certain aspects of the invention, especially where a ratio of isotopically labeled gas to non-isotopically labeled gas is used in the analysis, a Finnegan Delta Plus XL™ Mass Spectrometer may be used. Collection of exhaled gases may be effected using a standard gas collection bag, using a glass vial with a septum (the subject simply blows into the vial through the septum) or using any other method for collecting breaths from the subject. It is also noted that isotopically labeled nitrogen-15 present in the urine, serum or plasma of the patient from cleavage of isotopically labeled isoniazid may also be analyzed according to the present invention. A ratio of isotopically labeled nitrogen-15 to non-isotopically labeled nitrogen in the urine, serum or plasma sample after isoniazid administration may be determined and compared to control levels taken from urine, serum or plasma of the subject prior to isoniazid administration. Alternatively, a control group can be used to establish control levels of isotopically labeled compounds in urine, serum or plasma levels and appropriate ratios for comparison purposes.

In the present methods, isotopically labeled isoniazid and optionally, isotopically labeled urea may be administered orally or preferably, by a pulmonary (e.g. intratracheal) route of administration. In the case of oral administration, the isoniazid or urea, alone or in combination, are administered orally to a subject to be tested for evidence of *M. tuberculosis* infection. Isoniazid may be administered in standard oral dosage form, preferably as an immediate release dosage form or as an enteric dosage form (especially when administered in combination with urea), in combination with a pharmaceutically acceptable carrier, additive or excipient.

Oral formulations of urea may be formulated in enteric dosage form to promote release in the small intestine (duodenum, jejunum, ileum) or in combination with a urease inhibitor to inhibit the action of *H. pylori* urease on administered urea. Compounds such as acetohydroxamic acid (Lithostat), a bismuth salt such as bismuth nitrate, bismuth carbonate, bismuth salicylate or bismuth citrate, a proton pump inhibitor such omeprazole (Prilosec), esomeprazole (Nexium), lansoprazole (Prevacid), pantoprazole (Protonix) and rabeprazole sodium (Aciphex), or a natural product extract from *ranunculus repens*, can be coadministered to avoid any action by urease from *H. pylori* in the gastrointestinal tract, more specifically, the stomach.

Thus, the present invention also relates to pharmaceutical compositions in oral dosage forms comprising effective amounts of isotopically labeled isoniazid, and optionally, isotopically labeled urea and a urease inhibitor, in combination with a pharmaceutically acceptable carrier, additive, diluent, or excipient. Compositions for oral administration include powders or granules, suspensions or solutions in water or non-aqueous media, sachets, capsules or tablets. Thickeners, diluents, flavorings, dispersing aids, emulsifiers or binders may be desirable.

In preferred aspects of the invention, the isotopically labeled isoniazid and/or isotopically labeled urea is administered to the lungs of the subject via pulmonary administration, for example, intratracheal administration. The pharmaceutical compositions of the invention for pulmonary administration are usually used as inhalants. The compositions can be formed into dry powder inhalants, inhalant suspensions, inhalant solutions, encapsulated inhalants and like known forms of inhalants. Such forms of inhalants can be prepared by filling the pharmaceutical composition of the invention into an appropriate inhaler such as a metered-dose inhaler, dry powder inhaler, atomizer bottle, nebulizer etc. before use. Of the above forms of inhalants, powder inhalants may be preferable.

When the pharmaceutical compositions of the invention are used in the form of a powder, the mean particle diameter of the powder is not especially limited but, in view of the residence of the particles in the lungs, is preferably that the particles fall within the range of about 0.1 to 20 μm, and particularly about 1 to 5 μm. Although the particle size distribution of the powder pharmaceutical composition of the invention is not particularly limited, it is preferable that particles having a size of about 25 μm or more account for not more than about 5% of the particles, and preferably, 1% or less to maximize delivery into the lungs of the subject.

The pharmaceutical composition in the form of a powder of the invention can be produced by, for example, using the drying-micronization method, the spray drying method and standard pharmaceutical methodology well known in the art.

By way of example without limitation, according to the drying-pulverization method, the pharmaceutical composition in the form of a powder can be prepared by drying an aqueous solution (or aqueous dispersion) containing the isoniazid, urea, or mixtures thereof and excipients which provide for immediate release in pulmonary tissue and microparticulating the dried product. Stated more specifically, after dissolving (or dispersing) a pharmaceutically acceptable carrier, additive or excipient in an aqueous medium, isoniazid, urea or mixtures of isoniazid and urea in effective amounts are added and dissolved (or dispersed) by stirring using a homogenizer, etc. to give an aqueous solution (or aqueous dispersion). The aqueous medium may be water alone or a mixture of water and a lower alcohol. Examples of usable lower alcohols include methanol, ethanol, 1-propanol, 2-propanol and like water-miscible alcohols. Ethanol is particularly preferable. After the obtained aqueous solution (or aqueous dispersion) is dried by blower, lyophilization, etc., the resulting product is pulverized or microparticulated into fine particles using jet mills, ball mills or like devices to give a powder having the above mean particle diameter. If necessary, additives as mentioned above may be added in any of the above steps.

According to the spray-drying method, the pharmaceutical composition in the form of a powder of the invention can be prepared, for example, by spray-drying an aqueous solution (or aqueous dispersion) containing isoniazid, urea or mixtures thereof and excipients, additives or carriers for microparticulation. The aqueous solution (or aqueous dispersion) can be prepared following the procedure of the above drying-micronization method. The spray-drying process can be performed using a known method, thereby giving a powdery pharmaceutical composition in the form of globular particles with the above-mentioned mean particle diameter.

The inhalant suspensions, inhalant solutions, encapsulated inhalants, etc. can also be prepared using the pharmaceutical composition in the form of a powder produced by the drying-micronization method, the spray-drying method and the like, or by using a carrier, additive or excipient and isoniazid, urea or mixtures thereof that can be administered via the lungs, according to known preparation methods.

Furthermore, the inhalant comprising the pharmaceutical composition of the invention is preferably used as an aerosol. The aerosol can be prepared, for example, by filling the pharmaceutical composition of the invention and a propellant into an aerosol container. If necessary, dispersants, solvents and the like may be added. The aerosols may be prepared as 2-phase systems, 3-phase systems and diaphragm systems (double containers). The aerosol can be used in any form of a powder, suspension, solution or the like.

Examples of usable propellants include liquefied gas propellants, compressed gases and the like. Usable liquefied gas propellants include, for example, fluorinated hydrocarbons (e.g., CFC substitutes such as HCFC-22, HCFC-123, HFC-134a, HFC-227 and the like), liquefied petroleum, dimethyl ether and the like. Usable compressed gases include, for example, soluble gases (e.g., carbon dioxide, nitric oxide), insoluble gases (e.g., nitrogen) and the like.

The dispersant and solvent may be suitably selected from the additives mentioned above. The aerosol can be prepared, for example, by a known 2-step method comprising the step of preparing the composition of the invention and the step of filling and sealing the composition and propellant into the aerosol container.

As a preferred embodiment of the aerosol according to the invention, the following aerosol can be mentioned: Examples of the compounds to be used include isotopically labeled isoniazid, isotopically labeled urea or mixtures thereof. As propellants, fluorinated hydrocarbons such as HFC-134a, HFC-227 and like CFC substitutes are preferable. Examples of usable solvents include water, ethanol, 2-propanol and the like. Water and ethanol are particularly preferable. In particular, a weight ratio of water to ethanol in the range of about 0:1 to 10:1 may be used.

The aerosol of the invention contains excipient in an amount ranging from about 0.01 to about $10^4$ wt. % (preferably about 0.1 to $10^3$ wt. %), propellant in an amount of about $10^2$ to $10^7$ wt. % (preferably about $10^3$ to $10^6$ wt. %), solvent in an amount of about 0 to $10^6$ wt. % (preferably about 10 to $10^5$ wt. %), and dispersant in an amount of 0 to $10^3$ wt. % (preferably about 0.01 to $10^2$ wt. %), relative to the weight of isoniazid and/or urea which is included in the final composition.

The pharmaceutical compositions of the invention are safe and effective for use in the diagnostic methods according to the present invention. Although the dosage of the composition of the invention may vary depending on the type of active substance administered (isoniazid, urea or mixtures thereof) as well as the nature (size, weight, etc.) of the subject to be diagnosed, the composition is administered in an amount effective for allowing the pharmacologically active substance to be cleaved to cleavage products to be measured. For example, the composition is preferably administered such that the active ingredient can be given to a human adult in a dose of about 0.001 to about 100 mg, about 0.01 mg to about 25 mg, about 0.05 mg to about 15 mg, about 0.1 mg to about 10 mg, about 0.5 mg to about 5 mg, about 1 to about 3 mg, and given in a single dose The form of the pharmaceutical composition of the invention such as a powder, solution, suspension etc. may be suitably selected according to the type of substance to be administered and the action of a target enzyme on isoniazid and/or urea.

As an administration route, direct inhalation via the mouth using an inhaler is usually preferable. Since the pharmaceutical composition of the invention allows direct local administration into the airways and in particular, directly to pulmonary tissue, the active substance contained therein produces immediate effects. Furthermore, the composition is formulated as an immediate release product so that cleavage and analysis can begin soon after administration.

The following examples are exemplary only and are not to be construed to limit the present invention in any way.

EXAMPLES

Example 1

Determination of Dependency of 30/28 Mass Signal on Colony Forming Units (CFUs)

Figure 1:
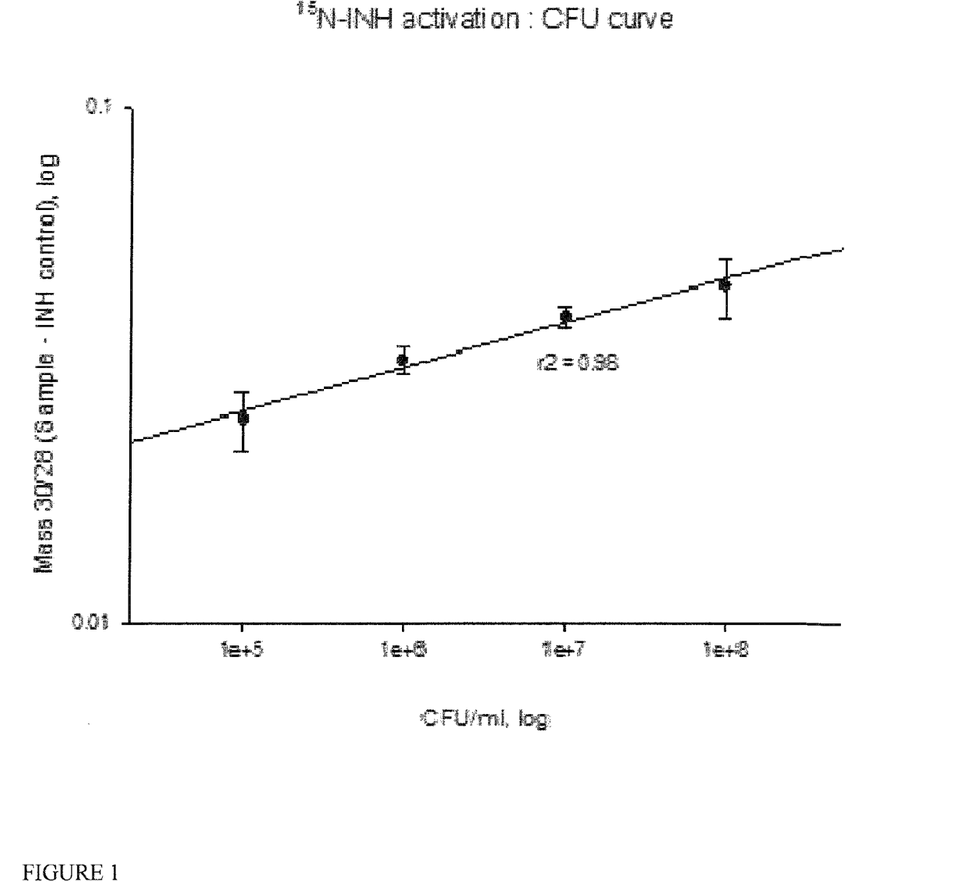
FIG. 1 depicts the results of testing to determine whether the 30/28 mass signal of one embodiment of the invention is CFU dependent.

*M. bovis* BCG (a tuberculosis bacteria strain) ($10^8$ CFU/mL, 3 mL) was incubated with $^{15}N_2$-hydrazyl-INH 1 mg/mL for 1 hour. Head gas (1 mL) was transferred to He-flushed tubes. Mass 30/28 in nitrogen gas was measured by IRMS. The $^{15}N_2$ signal (molecular weight–30 g/mol) as compared to the $^{14}N_2$ signal (molecular weight 28 g/mol) from control cultures treated with unenriched INH were subtracted. Numbers are mean values+/−STD (n=3). The signal was proportional to CFU/mL. The results are shown in FIG. 1.

Example 2

Determination of the Time Dependence of the 30/28 Mass Signal

Figure 2:
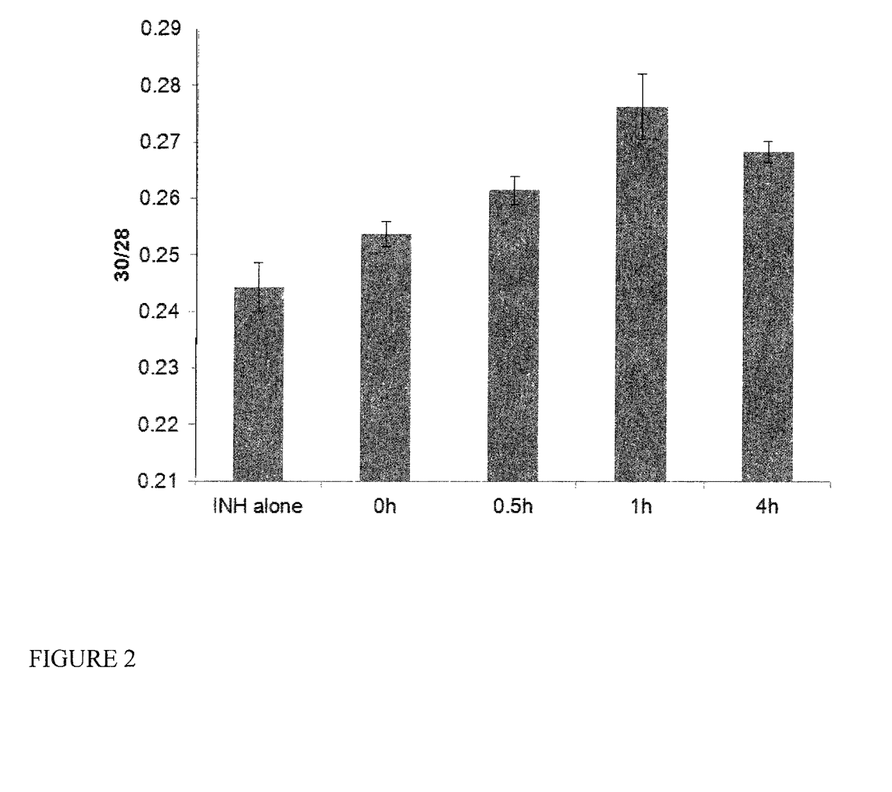
FIG. 2 depicts the results of testing to determine the time dependence of the 30/28 mass signal for one embodiment of the invention.

*M. bovis* BCG ($10^8$ CFU/mL, 3 mL) was incubated with $^{15}N_2$-hydrazyl-INH 1 mg/mL for differing time points. Head gas (1 mL) was transferred to He-flushed tubes. Mass 30/28 in nitrogen gas was measured by IRMS. No subtraction was performed. As shown in FIG. 2, there is an increase in the signal over the course of an hour, which then begins to decrease by 4 hours. Without wishing to be held to theory, this decrease may be attributable to the isoniazid killing the bacteria.

Example 3

Determination of the $^{15}N_2$-Hydrazyl-INH Dose Dependence of the 30/28 Mass Signal

Figure 3:
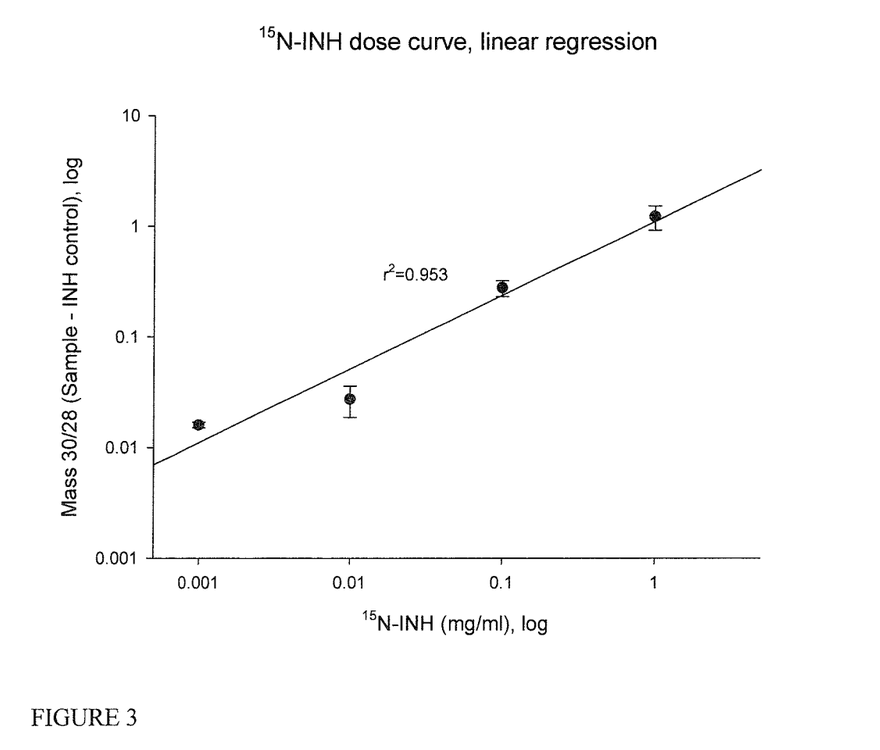
FIG. 3 depicts the results of testing to determine dose dependence of one embodiment of the invention of the 30/28 mass signal.

*M. bovis* BCG ($10^8$ CFU/ml, 3 mL) was incubated for 4 hours with differing concentrations of $^{15}N_2$-hydrazyl-INH. Head gas (1 mL) was transferred to He-flushed tubes. Mass 30/28 in nitrogen gas was measured by IRMS. The $^{15}N_2$ signal from control cultures treated with unenriched INH were subtracted. The signal was dependent upon dose. The results are shown in FIG. 3.

Example 4

Determination of Behavior of Virulent *Mycobacterium tuberculosis* H37Rv

Figure 4:
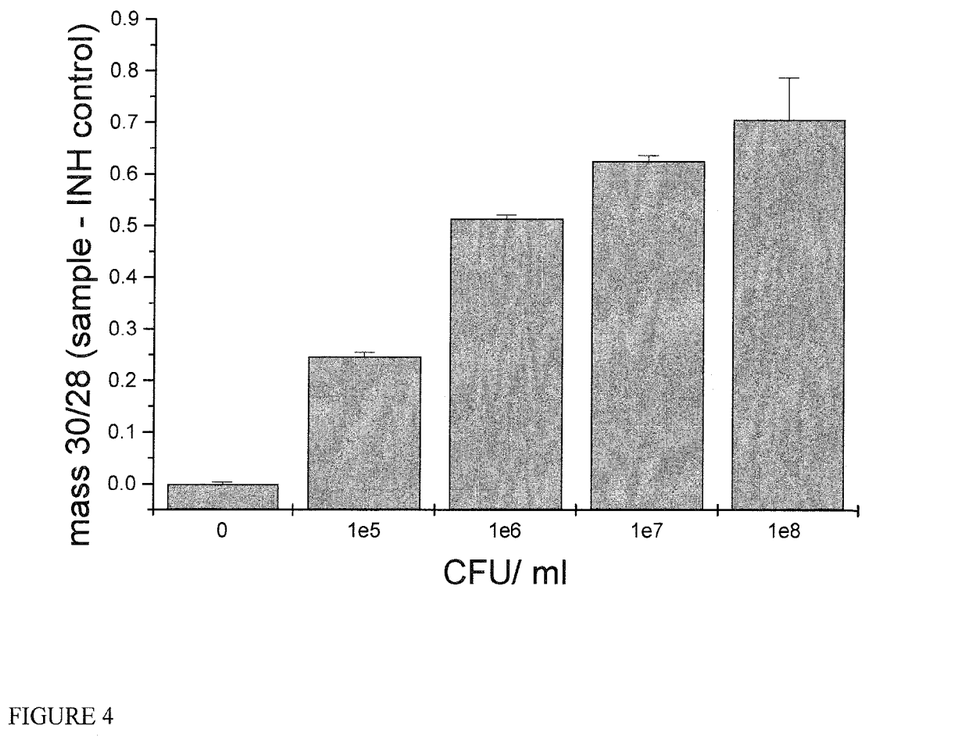
FIG. 4 depicts results of testing to determine behavior of virulent *M. tuberculosis* using one embodiment of the invention.

*Mycobacterium tuberculosis* H37Rv ($10^8$ CFU/ml, 3 mL) was incubated with $^{15}N_2$-hydrazyl-INH 1 mg/mL for 1 hour. Head gas (1 mL) was transferred to He-flushed tubes. Mass 30/28 in nitrogen gas was measured by IRMS. The $^{15}N_2$ signal from control cultures treated with unenriched INH were subtracted. Numbers are mean values+/−STD (n=3). The signal was proportional to CFU/mL. Results are depicted in FIG. 4.

Figure 5:
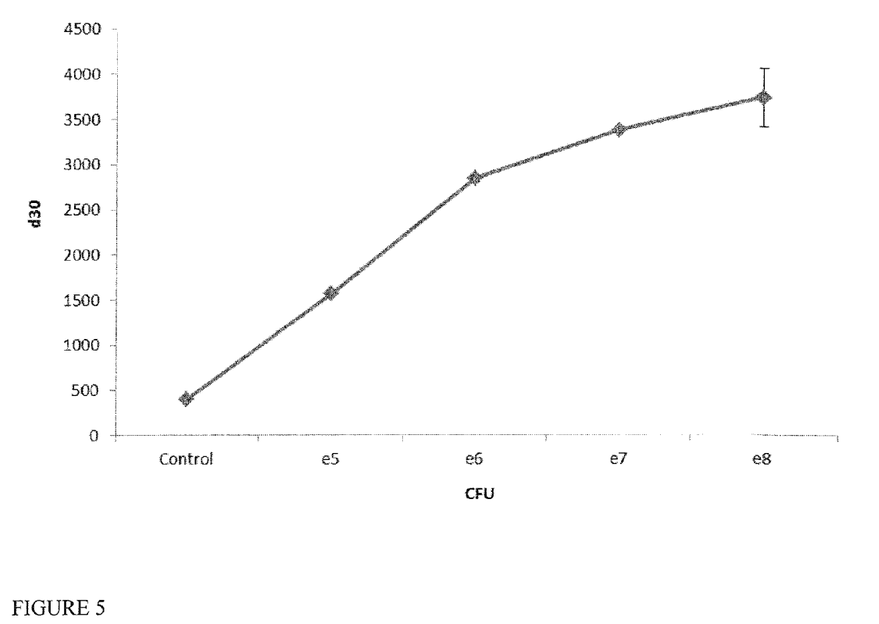
FIG. 5 depicts d30 in head gas produced by *M. tuberculosis* H37Rv with $^{15}N_2$—INH incubation.

Example 5 d30 in Head Gas Produced by *M. tuberculosis* H37Rv with 15N2-INH Incubation Mtb H37Rv [1×10(8) cfu/ml, 3 ml] was incubated with $^{15}$N—INH at 1 mg/ml (1,000 MIC) for 1 hr. Head gas (1 ml) was collected, filtered, and transferred to He-flushed tubes. d30 was measured by IRMS-GC. Numbers are mean values+/−STD (n=3). d30=[(sample mass ratio 30/28−ref gas 30/28)/ref gas 30/28]×1000. Ultra highly pure (>99.99%) N$_2$ gas was used as reference gas. One-way ANOVA, p=0.000. This experiment demonstrates that virulent tuberculosis produces $^{15}$N$_2$ in a density dependent manner. Results are depicted in FIG. 5.

Example 6

Comparison of Dd30: KatG Activity of H37Rv or S315T

Figure 6:
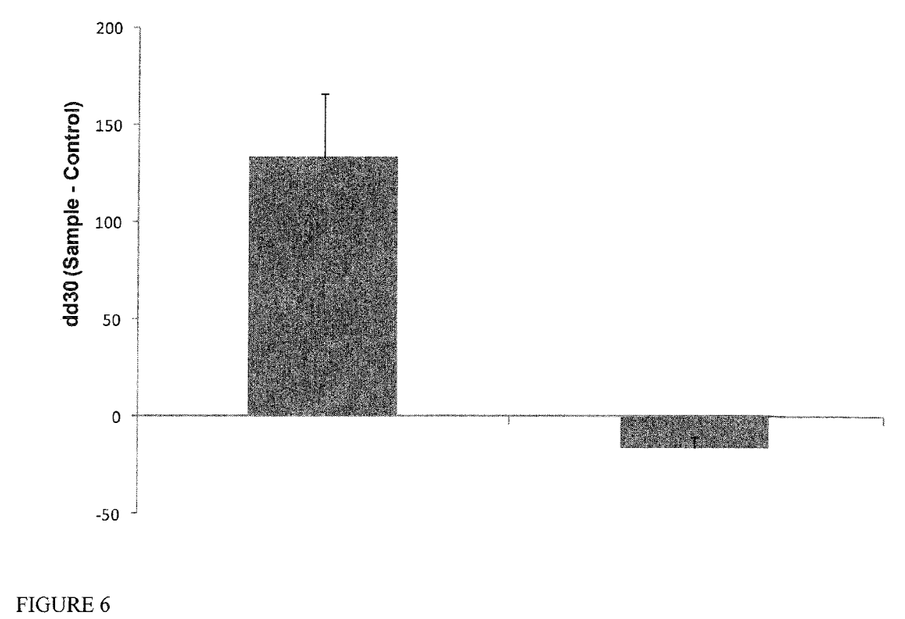
FIG. 6 depicts dd30 in head gas produced by NH-sensitive *M. tuberculosis* H37Rv or NH-resistant KatG S315T mutant, with $^{15}N_2$—INH incubation.

Mtb [1×10(8) cfu/ml, 3 ml] was incubated with 15N—INH at 1 mg/ml (1,000 MIC) for 1 hr. Head gas (1 ml) was collected, filtered, and transferred to He-flushed tubes. dd30 was measured by IRMS. Numbers are mean values+/−STD (n=3). dd30=d30(Sample)−d30(Control). d30=[(sample mass ratio 30/28−ref gas 30/28)/ref gas 30/28]×1000. Students' t test, p=0.005. This experiment demonstrates that INH resistance can be detected in vitro. Results are depicted in FIG. 6.

Example 7

Dd30 in Exhaled Gas from Rabbits after 15N2-INH Instillation

Figure 7:
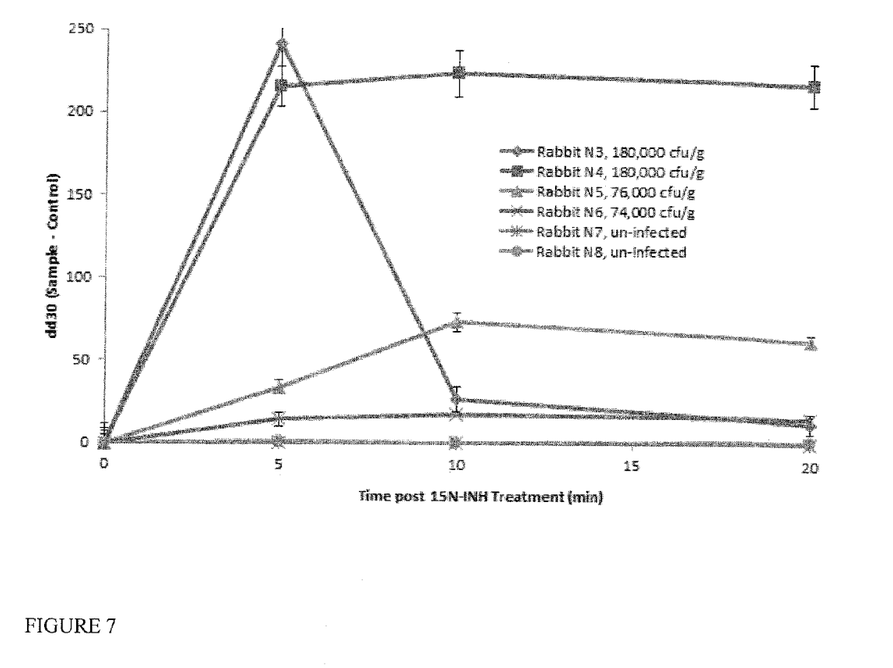
FIG. 7 depicts dd30 in exhaled gas from rabbits after $^{15}N_2$—INH instillation.

Infected animals give increase in dd30 signal, but uninfected rabbits do not. Rabbits (pathogen-free outbred New Zealand White) were infected with the indicated CFU of Mtb H37Rv in aerosol. At week 6, rabbits were anesthetized with ketamine (15-25 mg/kg) and xylazine (5-10 mg/kg), and treated with $^{15}$N—INH at 10 mg/400 ul PBS by intratracheal intubation. Exhaled breath gas (12 ml) was collected into Helium gas-flushed tubes at 0, 5, 10, and 20 min post $^{15}$N—INH administration. $^{15}$N$_2$ enrichment in breath gas was measured by IRMS-GC and presented by dd30. d30=[(sample mass ratio 30/28−ref gas 30/28)/ref gas 30/28]×1000. dd30=d30(Sample)−d30(Control). Ultra pure (>99.99%)$^{14}$N$_2$ gas was used as reference gas. Results are depicted in FIG. 7.

What is claimed:

1. A method for determining the presence or absence of a mycobacterial infection in the lungs of a patient comprising:
   administering to the lungs of the patient a diagnostically effective amount of $^{15}$N-labeled isoniazid and optionally, isotopically labeled urea;
   collecting one or more samples of exhaled breath from the subject; and
   determining an amount of $^{15}$N-labeled nitrogen gas in said samples;
   said amount indicating presence or absence of the mycobacterial infection in the lungs of the patient.

2. The method of claim 1 wherein the mycobacterial infection is a tuberculosis infection.

3. The method of claim 1, wherein the mycobacterial infection is a *Mycobacterium bovis* infection.

4. The method of claim 1, wherein the $^{15}$N-labeled isoniazid is

5. The method of claim 1, wherein said samples are collected for a predetermined time.

6. The method of claim 1, wherein the determining comprises comparing the ratio of $^{15}$N-labeled nitrogen gas to unlabeled nitrogen gas in said samples to the ratio of $^{15}$N-labeled nitrogen gas to unlabeled nitrogen gas in a sample obtained from the patient prior to the administration of the $^{15}$N-labeled isoniazid.

7. The method of claim 6, wherein an increase in the ratio of $^{15}$N-labeled nitrogen gas to unlabeled nitrogen gas in said samples to the ratio of $^{15}$N-labeled nitrogen gas to unlabeled nitrogen gas in the sample obtained from the patient prior to the administration of the isotopically labeled isoniazid is indicative of the presence of the mycobacterial infection.

8. The method of claim 1, wherein mycobacteria of the mycobacterial infection have an active KatG enzyme.

* * * * *